United States Patent
Germann et al.

Patent Number: 6,080,742
Date of Patent: Jun. 27, 2000

[54] SUBSTITUTED BENZAMIDES

[75] Inventors: Tieno Germann, Herzogenrath; Stefanie Frosch, Aachen; Oswald Zimmer, Wuerselen, all of Germany

[73] Assignee: Gruenenthal GmbH, Aachen, Germany

[21] Appl. No.: 09/405,180

[22] Filed: Sep. 24, 1999

[30] Foreign Application Priority Data

Sep. 24, 1998 [DE] Germany .................. 198 43 793

[51] Int. Cl.⁷ .............. A61K 31/45; A61K 31/5377; C07D 401/06; C07D 413/06
[52] U.S. Cl. .............. 514/235.5; 514/316; 514/328; 544/130; 546/188; 546/220
[58] Field of Search .............. 544/130; 546/188, 546/220; 514/235.5, 316, 328

[56] References Cited

PUBLICATIONS

Audit, CA 122:23705, 1995.
Trembleau, S., Germann, T., Gately, M., and Adorini, L. (1995) "The Role of IL–12 in the Induction of Organ–Specific Autoimmune Diseases". *Immunol. Today* 16:383–386.
Mueller, G., Saloga, J., Germann, T., Schuler, G., Knop. J., and Enk, H. (1995) "IL–12 as Mediator and Adjuvant for the Induction of Contact Sensitivity In Vivo". *J. Immunol.* 155:4661–4668.
Neurath, M., Fuss, I., Kelsall, B., Stueber, E., and Strober, W. (1995) "Antibodies to Interleukin 12 Abrogate Established Experimental Colitis in Mice". *J. Exp. Med.* 182:1281–1290.
Segal, B., Dwyer, B., and Shevach, E. (1998) "An Interleukin (IL)–10/IL–12 Immunoregulatory Circuit Controls Susceptibility to Autoimmune Disease". *J. Exp. Med.* 187:537–546.
Powrie, F. (1995) "T Cells in Inflammatory Bowel Disease: Protective and Pathogenic Roles". *Immunity* 3:171–174.
Rudolphi, A., Bonhagen, K., and Reimann, J. (1996) "Polyclonal Expansion of Adoptively Transferred CD4+ αβ T Cells in the Colonic Lamina Propria of Scid Mice with Colitis". *Eur. J. Immunol.* 26:1156–1163.

Bregenholt, S. and Claesson, M. (1998) "Increased Intracellular Th1 Cytokines in Scid Mice with Inflammatory Bowel Disease". *Eur. J. Immunol.* 28:379–389.
Chernoff, A., Granowitz, E., Shapiro, L., Vannier, E., Lonnemann, G., Angel, J., Kennedy, J., Rabson, A., Wolff, S., and Dinarello, C. (1995) "A Randomized, Controlled Trial of IL–10 in Humans". *J. Immunol.* 154:5492–5499.
Van Deventer, S., Elson, C., and Fedorak, R. (1997) "Multiple Doses of Intravenous Interleukin 10 in Steroid–Refractory Crohn's Disease". *Gastroenterology* 113:383–389.
Asadullah, K., Sterry, W., Stephanek, K., Jasulaitis, D., Leupold, M., Audring, H., Volk, H., and Doecke, W. (1998) "IL–10 is a Key Cytokine in Psoriasis". *J. Clin. Invest.* 101:783–794.
Moller et al., "Inhibition of IL–12 Production by Thalidomide", *J. Immunol.* 159:5157–61 (1997).

*Primary Examiner*—Laura L. Stockton
*Attorney, Agent, or Firm*—Evenson, McKeown, Edwards & Lenahan, P.L.L.C.

[57] ABSTRACT

Substituted benzamides corresponding to the formula I

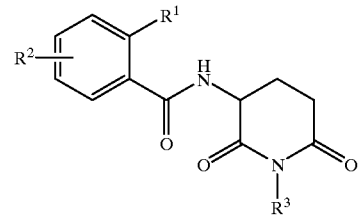

wherein $R^1$, $R^2$ and $R^3$ have the meanings given herein, and their use in pharmaceutical compositions. The compounds are particularly useful as immunomodulators.

4 Claims, No Drawings

SUBSTITUTED BENZAMIDES

BACKGROUND OF THE INVENTION

This invention relates to substituted benzamides corresponding to the general formula I

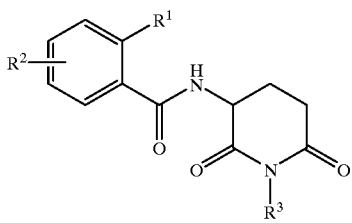

and their use in medicaments.

Autoimmune diseases arise as a result of a reaction of the immune system against endogenous structures. In the course of this the normally present tolerance towards endogenous tissues is suspended. Antibodies, and in particular T-lymphocytes and monocytes/macrophages, play an important part in the pathogenesis of the various autoimmune diseases. Activated monocytes/macrophages secrete a multitude of different inflammatory intermediaries, which are directly or indirectly responsible for the breakdown of the tissues affected by the autoimmune disease. The activation of the monocytes/macrophages is mediated either by the interaction with T-lymphocytes or by bacterial products such as lipopolysaccharide (LPS). The activation of monocytes/macrophages and of granulocytes induced by various bacterial products is moreover characteristic of inflammatory reactions in general.

The importance of the equilibrium between inflammatory (for example, interleukin IL-12) and anti-inflammatory cytokines (for example, interleukin IL-10) for the development and progress of inflammation and autoimmune diseases is clearly documented because of numerous experiments on animals and initial clinical trials. The pathophysiological significance of IL-12 is apparent in various animal models for diseases such as rheumatoid arthritis, multiple sclerosis, diabetes mellitus, as well as inflammatory diseases of the skin and mucous membranes (Immunol. Today 16/8: 383–387, 1995; J. Immunol. 155: 4661–4668, 1995; J. Exp. Med. 182: 1281–1290, 1995; J. Exp. Med. 187/4: 537–546, 1998). The respective diseases were triggered by the application of IL-12 and an abatement of the course of the disease, extending to a recovery of the animals, was apparent after neutralisation of endogenous IL-12.

In inflammatory bowel diseases, both in diseased animals and in patients suffering from Crohn's disease, there is a distinctly increased T-cell reactivity in the inflamed sections of the gut. This T-cell reactivity is characterised by the increased expression of IL-12 and IFN- in the lesions. On the other hand, the immunosuppressive cytokine IL-10 is clearly diminished in the lesions (Immunity 3: 171–174, 1995; J. Exp. Med. 182: 1281–1290, 1995; Eur. J. Immunol. 26: 1156–1163; Eur. J. Immunol. 28: 379–389, 1998). The importance of the immunosuppressive cytokine IL-10 for the development of inflammatory intestinal diseases is also apparent from the fact that IL-10 knockout mice develop a spontaneous colitis (Immunity 3: 171–174, 1995). The activation of the IFN-y-producing T-cells in the lamina propria of the intestine depends substantially on the local formation of IL-12. Antibodies to IL-2 abrogate established experimental colitis in mice. The neutralization of IL-12 by antibodies led to a striking improvement in both the clinical and histopathological aspects of the disease within a few days. No IFN-γ production could be detected in in vitro activated T-cells from the lamina propria of mice which received anti-IL-12 treatment (J. Exp. Med. 182: 1281–1290).

Application of recombinant IL-10 in humans confirms the anti-inflammatory properties. Following the administration of IL-10 to healthy subjects, the formation of the inflammatory cytokines TNF-α and IL-1 by monocytes activated ex vivo with LPS is reduced by 65 to 95% (J. Immunol. 154: 5492–5499, 1995). The use of IL-10 in patients suffering from steroid-refractory Crohn's disease resulted in an improvement in the clinical symptoms (Gastroenterology, 113: 383–389). Recently, the subcutaneous application of IL-10 to three patients suffering from psoriasis was also reported. There was a marked improvement in the symptoms of the disease. Moreover, the formation of IL-12 and TNF as well as the expression of surface molecules on monocytes were also decreased (J. Clin. Invest. 101: 783–794). The use of antibodies against IL-12 in humans is now imminent.

In summary, it can be stated that a deficiency of IL-10 or an excess of IL-12 determines the pathophysiology of a multitude of inflammatory diseases. Attempts to normalize the IL-10/IL-12 balance therefore have a great therapeutic potential.

SUMMARY OF THE INVENTION

Consequently, the object of this invention was the development of new immunomodulators which do not lead to a general immunosuppression but effect a normalization of the IL-10/IL-12 balance.

It has now been found that the requirements placed on the substances to be developed are met by specific substituted benzamides.

Accordingly, the invention provides substituted benzamides corresponding to formula I

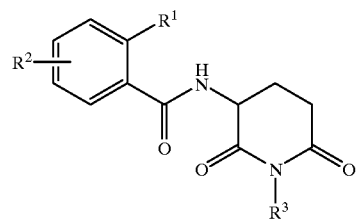

wherein
$R^1$ represents a group corresponding to the formula $COOR^4$, wherein $R^4$ denotes a straight-chain or branched alkyl group having 1 to 6 carbon atoms, or a group corresponding to the formula $CONR^5R^6$, wherein $R^5$ and $R^6$ are identical or different and denote an alkyl group having 1 to 6 carbon atoms (straight-chain or branched) or, together with the N atom, denote a pyrrolidine, piperidine, hexamethyleneimine or morpholine ring;
$R^2$ denotes chlorine, fluorine, $CF_3$, an alkyl group having 1 to 3 carbon atoms or hydrogen; and
$R^3$ denotes the hydroxyl group, an alkyl or alkoxy group having 1 to 6 carbon atoms (straight-chain or branched and optionally substituted with OH—, an alkoxy group, ester group or an open-chain or cyclic amide group having 1 to 6 carbon atoms) or a group $CH_2$—$NR^5R^6$, wherein $R^5$ and $R^6$ are as defined above.

The compounds according to the invention can be in racemic form or in enantiomerically pure form or in the form of salts with pharmaceutically compatible salts.

DESCRIPTION OF PREFERRED EMBODIMENTS

Preferred substituted benzamides are those in which the group $R^1$ represents a group corresponding to the formula $COOR^4$, wherein $R^4$ denotes a straight-chain or branched alkyl group having 1 to 6 carbon atoms, or a group corresponding to the formula $CONR^5R^6$, wherein $R^5$ and $R^6$ together with the N atom denote a morpholine ring; R2 is H and $R^3$ denotes the hydroxyl group or a group $CH_2$—$NR^5R^6$, wherein $R^1$ and $R^6$ together with the N atom denote a morpholine ring.

The 2-(morpholino-4-carbonyl)-N-(1-morpholin-4-ylmethyl-2,6-dioxopiperidin-3-yl)benzamide and the N-(1-hydroxy-2,6-dioxopiperidin-3-yl) phthalamic acid-methyl ester, are particularly preferred.

Compounds corresponding to the general formula I can be obtained by first of all converting, in known manner, a carboxylic acid corresponding to formula IIa or IIb

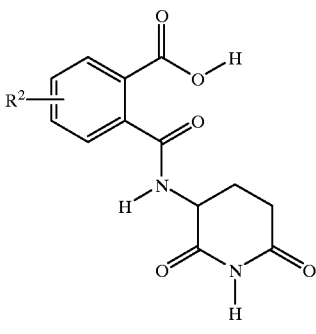

IIa

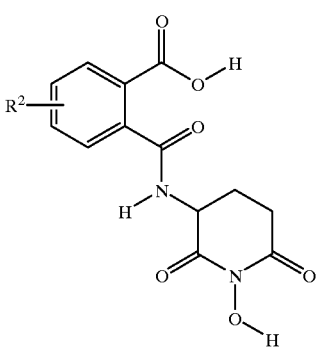

IIb into an ester ($R^1$=$COOR^4$) or into an amide ($R^1$=$CONR^5R^6$). Compounds according to the invention are thus already obtained starting from the carboxylic acid IIb. The group $R^3$ which does not denote the hydroxyl group can then be introduced into these compounds derived correspondingly from the carboxylic acid IIa, again in known manner, for example, by Mannich reaction with paraformaldehyde and a secondary amine corresponding to the formula $HNR^5R^6$.

The invention also provides the use of the substituted benzamides corresponding to formula I as medicaments, in particular as immunomodulators. The substances according to the invention clearly inhibit the production of the inflammatory cytokine IL-12 by LPS-activated human monocytes. On the other hand, substances of this group increase the production of the anti-inflammatory cytokine IL-10 by LPS-activated human monocytes. This distinguishes the new substances from known immunomodulators such as steroids and phosphodiesterase inhibitors, which suppress the synthesis of IL-12 as well as that of IL-10. Due to their characteristic immunomodulatory activity (inhibition of IL-12, increase of IL-10), the substances according to the invention are suitable for the treatment and/or prophylaxis of inflammation, in particular inflammation of the skin and mucous membranes and of the vessels, as well as for the treatment and/or prophylaxis of autoimmune diseases.

These diseases include, inter alia, inflammation of the skin (for example, atopic dermatitis, psoriasis, eczema), inflammation of the respiratory tract (for example, bronchitis, pneumonia, bronchial asthma, ARDS (adult respiratory distress syndrome), sarcoidosis, silicosis/fibrosis), inflammation of the gastrointestinal tract (for example, gastroduodenal ulcer, Crohn's disease, ulcerative colitis), also diseases such as hepatitis, pancreatitis, appendicitis, peritonitis, nephritis, aphthous ulcers, conjunctivitis, keratitis, uveitis, rhinitis.

The autoimmune diseases include, for example, diseases of the arthritic type (for example, rheumatoid arthritis, HLA-B27 associated diseases), also multiple sclerosis, juvenile diabetes or lupus erythematosus.

Further indications are sepsis, bacterial meningitis, cachexia, transplant rejection reactions, graft-versus-host reactions as well as reperfusion syndrome and atherosclerosis.

Medicaments according to the invention contain at least one compound corresponding to the general formula I and in addition carriers, fillers, solvents, diluents, dyes and/or binders. The selection of the auxiliary substances and the quantities to be used depend on whether the medicament is to be administered orally, intravenously, intraperitoneally, intradermally, intramuscularly, intranasally, buccally or locally. Suitable preparations for oral administration are in the form of tablets, chewing tablets, dragees, capsules, granules, droplets, juices or syrups. Solutions, suspensions, readily reconstitutable dry preparations and sprays are suitable for parenteral and topical administration and for inhalation. Compounds according to the invention in a depot in dissolved form, on a supporting film or a plaster, optionally with the addition of agents which promote penetration of the skin, are examples of suitable percutaneous forms of administration. Delayed release of the compounds according to the invention from orally or percutaneously administrable forms of preparation is also possible.

The quantity of active ingredient to be administered to patients varies depending on the weight of the patient, on the method of administration, the indication and the severity of the disease. Generally, 1 to 150 mg/kg of at least one compound according to the invention corresponding to formula I is administered.

EXAMPLES

TABLE 1

| Example No. | Structure of substance Formula I with | | Name |
|---|---|---|---|
| 1 (Comparison Example) | $R^1$ = | COOH | N-(1-morpholin-4-ylmethyl-2,6-dioxopiperidin-3-yl)phthalamic acid |
| | $R^2$ = | H | |
| | $R^3$ = | $CH_2$—$NR^5R^6$, wherein $R^5$ and $R^6$ together with the N atom denote a morpholine ring | |
| 2 (Comparison | $R^1$ = | H | N-(1-morpholin-4-ylmethyl-2,6- |
| | $R^2$ = | H | |

TABLE 1-continued

| Example No. | Structure of substance Formula I with | | Name |
|---|---|---|---|
| Example) | $R^3$ = | $CH_2$—$NR^5R^6$, wherein $R^5$ and $R^6$ together with the N atom denote a morpholine ring | dioxopiperidin-3-yl)benzamide |
| 3 (according to the invention) | $R^1$ = | $CONR^5R^6$, wherein $R^5$ and $R^6$ together with the N atom denote a morpholine ring | 2-(morpholine-4-carbonyl)-N-(1-morpholin-4-ylmethyl-2,6-dioxopiperidin-3-yl)benzamide |
| | $R^2$ = | H | |
| | $R^3$ = | $CH_2$—$NR^5R^6$, wherein $R^5$ and $R^6$ together with the N atom denote a morpholine ring | |
| 4 (according to the invention) | $R^1$ = | $COOCH_3$ | N-(1-hydroxy-2,6-dioxoperidin-3-yl)phthalamic acid-methyl ester |
| | $R^2$ = | H | |
| | $R^3$ = | OH | |
| 5 (according to the invention) | $R^1$ = | $CONR^5R^6$, wherein $R^5$ and $R^6$ together with the N atom denote a morpholine ring | 2-(morpholine-4-carbonyl)-N-(1-piperidin-4-ylmethyl-2,6-dioxopiperidin-3-yl)benzamide |
| | $R^2$ = | H | |
| | $R^3$ = | $CH_2$—$NR^5R^6$, wherein $R^5$ and $R^6$ together with the N atom denote a piperidine ring | |
| 6 (according to the invention) | $R^1$ = | $COOC_2H_5$ | N-(2,6-dioxo-1-piperidin-1-yl-methyl-piperidin-3-yl)phthalamic acid-ethyl ester |
| | $R^2$ = | H | |
| | $R^3$ = | $CH_2$—$NR^5R^6$, wherein $R^5$ and $R^6$ together with the N atom denote a piperidine ring | |

The substances in Table 1 were analyzed by $^1$H-NMR spectroscopy (equipment: DPX 300 Avance, from the firm Bruker; 300 MHz; solvent: DMSO-$d_6$; data on chemical shifts in ppm).

Example 1

1.97–2.16 (m, 2H, $CH_2$); 2.52–2.86 (m, 2H, $CH_2$) 3.20–3.75 (m, 8H, $CH_2$); 4.50–4.65 (m, 2H, $NCH_2N$) 4.64–4.82 (m, 1H, CH); 7.49–7.66 (m, 3H, aromat.); 7.79–7.85 (d, 1H, aromat.); 8.60–8.72 (d, 1H, CONH).

Example 2

1.94–2.20 (m, 2H, $CH_2$); 2.68–2.95 (m, 2H, $CH_2$); 3.28–3.70 (m, 8H, $CH_2$); 4.52–4.65 (m, 2H, $NCH_2N$); 4.83–4.96 (m, 1H, CH); 7.42–7.58 (m, 3H, aromat.); 7.85–7.92 (m, 2H, aromat.); 8.85–8.89 (d, 1H, CONH).

Example 3

1.92–2.24 (m, 2H, $CH_2$); 2.69–3.02 (m, 2H, $CH_2$); 3.12 (s, 2H, $CH_2$); 3.35–3.77 (m, 12H, $CH_2$) 4.52–4.68 (m, 2H, $NCH_2N$); 4.74–4.98 (m, 1H, CH); 7.28–7.32 (d, 1H, aromat.); 7.45–7.59 (m, 2H, aromat.); 7.74–7.80 (d, 1H, aromat.); 8.78–8.88 (d, 1H, CONH).

Example 4

2.01–2.18 (m, 2H, $CH_2$); 2.58–2.88 (m, 2H, $CH_2$); 3.79 (s, 3H, $COOCH_3$); 4.70–4.80 (m, 1H, CH); 7.54–7.72 (m, 3H, aromat.); 7.77–7.81 (d, 1H, aromat.); 8.77–8.82 (d, 1H, CONH); 10.21 (s, 1H, NOH).

Example 5

1.38–1.46 (m, 6H, $CH_2$); 1.96–2.16 (m, 2H, $CH_2$); 2.20–2.32 (m, 4H, $CH_2$); 2.60–2.92 (m, 2H, $CH_2$); 3.26–3.75 (m, 8H, $CH_2$); 4.57–4.70 (m, 2H, $NCH_2N$) 4.72–4.88 (m, 1H, CH); 7.28–7.30 (d, 1H, aromat.); 7.43–7.57 (m, 2H, aromat.); 7.70–7.74 (m, 1H, aromat.); 8.75–8.78 (d, 1H, CONH).

Example 6

1.18–1.26 (t, 3H, $CH_3$); 1.36–1.48 (m, 6H, $CH_2$); 1.95–2.16 (m, 2H, $CH_2$); 2.22–2.34 (m, 4H, $CH_2$); 2.60–2.90 (m, 2H, $CH_2$); 4.08–4.18 (q, 2H, $OCH_2$); 4.55–4.68 (m, 2H, $NCH_2N$); 4.70–4.80 (m, 1H, CH); 7.54–7.72 (m, 3H, aromat.); 7.78–7.83 (d, 1H, aromat.); 8.78–8.82 (d, 1H, CONH).

Investigation of the immunomodulatory activity

Human monocytes were isolated from peripheral blood mononuclear cells (PBMC), which had been obtained from heparinized whole blood by means of a Ficoll density-gradient centrifugation. To this end, the PBMC were incubated with a monoclonal antibody which was directed against the monocyte-specific surface molecule CD14 and to which superparamagnetic microbeads (Miltenyi Biotech, Bergisch Gladbach) were coupled. To effect a positive selection of the labelled monocytes from the cell mixture of the PBMC, the total cell suspension was applied to a column with ferromagnetic supporting matrix and this was placed in a magnetic field. By this means the cells, which were labelled with microbeads, were bound to the supporting matrix, unlabelled cells passed through the column and were discarded. After the removal of the matrix out of the magnetic field, the cells labelled with antibodies were eluted by rinsing the now demagnetised column with a buffer. The purity of this CD14-positive monocyte population thus obtained was about 95 to 98%. These monocytes were incubated—at a density of $10^6$ cells/ml culture medium (RPMI, supplemented with 10% foetal calf serum)—together with the test substances dissolved in DMSO, for one hour at 37° C. and 5% $CO_2$. Then 20 μg/ml LPS from E. coli was added thereto. After 24 hours, cell-free culture supernatants were taken and analyzed to determine the content of the cytokines IL-12 and IL-10.

The concentration of IL-12 and IL-10 in the cell culture supernatants was determined by means of sandwich-ELISAs using two anti-IL-12 and anti-IL-10 monoclonal antibodies (Biosource Europe, Fleurus, Belgium). A standard reference curve for human IL-12 and IL-10 respectively was included. The detection limit of the IL-12 ELISA was 10 pg/ml and that of the IL-10 ELISA was 15 pg/ml.

TABLE 2

Influence of the test substances on the production of IL-12 and IL-10 by LPS-activated monocytes.

| Substance | Concentration | IL-12 production % of the control (=100%) | IL-10 production % of the control (=100%) |
|---|---|---|---|
| from Example 1 | 10 μg/ml | 76 | 109 |
|  | 2 μg/ml | 78 | 84 |
|  | 0.4 μg/ml | 90 | 87 |
| from Example 2 | 6.0 μg/ml | 105 | 69 |
|  | 2.0 μg/ml | 104 | 99 |
|  | 0.66 μg/ml | 102 | 109 |
|  | 0.22 μg/ml | 99 | 114 |
| from Example 3 | 10 μg/ml | 30 | 127 |
|  | 2 μg/ml | 46 | 121 |
|  | 0.4 μg/ml | 87 | 108 |
| from Example 3 (second test) | 6.0 μg/ml | 49 | 131 |
|  | 2.0 μg/ml | 53 | 133 |
|  | 0.66 μg/ml | 59 | 123 |
|  | 0.22 μg/ml | 64 | 117 |
| from Example 4 | 10 μg/ml | 23 | 112 |
|  | 2 μg/ml | 40 | 189 |
|  | 0.4 μg/ml | 66 | 122 |
| from Example 5 | 6.0 μg/ml | 47 | 134 |
|  | 2.0 μg/ml | 57 | 134 |
|  | 0.66 μg/ml | 67 | 122 |
|  | 0.22 μg/ml | 88 | 115 |
| from Example 6 | 6.0 μg/ml | 38 | 130 |
|  | 2.0 μg/ml | 47 | 124 |
|  | 0.66 μg/ml | 61 | 132 |
|  | 0.22 μg/ml | 79 | 102 |
| Dexamethasone | 1 μM | 6 | 34 |
|  | 0.1 μM | 6 | 35 |
|  | 0.01 μM | 20 | 64 |
|  | 0.001 μM | 83 | 105 |
| Pentoxifylline | 50 μg/ml | 74 | 74 |
|  | 5 μg/ml | 72 | 81 |
| Rolipram | 50 μM | 32 | 28 |
|  | 0.5 μM | 30 | 79 |
|  | 0.005 μM | 58 | 92 |

The results presented in Table 2 show that known immunomodulators such as dexamethasone, pentoxifylline and Rolipram suppress both the production of IL-12 and that of IL-10 by LPS-activated monocytes. In comparison, structurally similar benzamides substituted with carboxyl groups (Example 1) exhibit only a slight action at high doses.

Surprisingly, the esters according to the invention (Examples 4 and 6) and the amides according to the invention (Examples 3 and 5) of the substituted benzamides exhibit immunomodulatory activity in the model investigated. Such compounds powerfully inhibit the synthesis of IL-12 by LPS-activated monocytes at concentrations of 10, 6 and 2 μg/ml, respectively. Unlike the known immunomodulators, they also increase the synthesis of IL-10. This characteristic pattern (clear inhibition of IL-12, increase of IL-10 in the same concentration range of substances) distinguishes a new type of immunomodulator.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A substituted benzamide corresponding to formula I

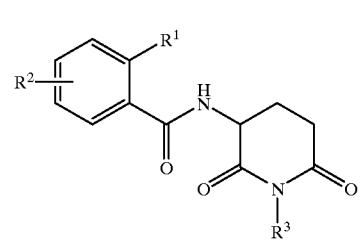

wherein $R^1$ represents a group corresponding to the formula $COOR^4$, wherein $R^4$ denotes a straight-chain or branched alkyl group having 1 to 6 carbon atoms, or a group corresponding to the formula $CONR^5R^6$, wherein $R^5$ and $R^6$ are identical or different and denote a straight-chain or branched alkyl group having 1 to 6 carbon atoms or, together with the N atom, denote a pyrrolidine, piperidine, hexamethyleneimine or morpholine ring;

$R^2$ denotes chlorine, fluorine, $CF_3$, an alkyl group having 1 to 3 carbon atoms or hydrogen, and $R^3$ denotes the hydroxyl group, a straight-chain or branched alkyl or alkoxy group having 1 to 6 carbon atoms and optionally substituted with OH—, an alkoxy group, ester group or an open-chain or cyclic amide group having 1 to 6 carbon atoms, or $R^3$ denotes a group $CH_2$—$NR^5R^6$, wherein $R^5$ and $R^6$ are as defined above.

2. A substituted benzamide according to claim 1, wherein $R^1$ represents a group corresponding to the formula $COOR^4$, wherein $R^4$ denotes a straight-chain or branched alkyl group having 1 to 6 carbon atoms, or a group corresponding to the formula $CONR^5R^6$, wherein $R^5$ and $R^6$ together with the N atom denote a morpholine ring;

$R^2$ is H, and $R^3$ denotes the hydroxyl group or a group $CH_2$—$NR^5R^6$, wherein $R^5$ and $R^6$ together with the N atom denote a morpholine ring.

3. A pharmaceutical composition comprising an effective immunomodulating amount of a substituted benzamide according to claim 1, and at least one pharmaceutical carrier or adjuvant.

4. A method of treating a patient suffering from a deficiency of IL-10 or an excess of IL-12, said method comprising the step of administering to said patient an effective immunomodulating amount of a substituted benzamide according to claim 1.

* * * * *